United States Patent
Dietz (10) Patent No.: US 10,962,615 B2
(45) Date of Patent: Mar. 30, 2021

(54) MAGNETIC RESONANCE DEVICE AND METHOD FOR PRODUCING A DIFFUSION GRADIENT COIL

(71) Applicant: Siemens Healthcare GmbH, Erlangen (DE)

(72) Inventor: Peter Dietz, Fuerth (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/527,982

(22) Filed: Jul. 31, 2019

(65) Prior Publication Data

US 2020/0041590 A1 Feb. 6, 2020

(30) Foreign Application Priority Data

Jul. 31, 2018 (EP) ..................... 18186548

(51) Int. Cl.
*G01R 33/385* (2006.01)
*A61B 5/055* (2006.01)

(52) U.S. Cl.
CPC ........ *G01R 33/3858* (2013.01); *A61B 5/0555* (2013.01); *G01R 33/3856* (2013.01)

(58) Field of Classification Search
CPC ............ G01R 33/3858; G01R 33/3856; G01R 33/56341; A61B 5/0555
See application file for complete search history.

(56) References Cited

U.S. PATENT DOCUMENTS

| 5,372,137 A | 12/1994 | Wong et al. |
| 5,600,245 A | 2/1997 | Yamamoto et al. |
| 2012/0259199 A1* | 10/2012 | Huwer ............. G01R 33/56341 600/410 |
| 2013/0335080 A1* | 12/2013 | Jo ...................... G01R 33/4824 324/309 |

OTHER PUBLICATIONS

Green Dan et al; "Hemispherical gradient coils for magnetic resonance imaging"; Magnetic Resonance in Medicine; VCol.: 54; No. 3; pp. 656-668; XP055549089; 2005.
Schenck, John et al; "Magnetic Forces and Torques on Local Gradient Coils: An Example Using a Head Gradient Coil"; Proceedings of the International Society for Magnetic Resonance in Medicine, ISMRM, 9th Scientific Meeting and Exhibition, Glasgow, Scotland; XP040583010; 2001.

(Continued)

*Primary Examiner* — Susan S Lee
(74) *Attorney, Agent, or Firm* — Schiff Hardin LLP (57) ABSTRACT

A magnetic resonance device is disclosed including a patient receiving zone, at least one diffusion gradient coil, at least one magnet for generating a basic magnetic field, and a plurality of gradient coils for generating gradient fields overlaying the basic magnetic field. The basic magnetic field extends substantially along a first direction in the patient receiving zone and a first gradient of a first gradient field runs in the first direction and at least one further gradient of a further gradient field runs in a further direction orthogonal to the first direction. The diffusion gradient coil has at least one conductor loop running in one plane or a plurality of conductor loops each running in parallel planes.

16 Claims, 3 Drawing Sheets

(56) References Cited

OTHER PUBLICATIONS

Dennis L. Parker et al; "Magnetic resonance imaging with composite (dual) gradients"; Concepts in Magnetic Resonance Part B (Magnetic Resonance Engineering); vol. 35B; No. 2; Seiten 89-97; XP055549191, ISSN: 1552-5031; DOI: 10.1002/cmr.b.20134; 2009.
Hidalgo-Tobon, Silvia S.; "Theory of gradient coil design methods for magnetic resonance imaging"; Concepts in Magnetic Resonance Part A; vol. 36A; No. 4; pp. 223-242; XP055183938; ISSN: 1546-6086; DOI: 10.1002/cmr.a.20163; 2010.
Van Der Velden, Tijl A et al; "Concurrent use of 4 gradient axis enables eddy current compensation of an unshielded gradient insert coil"; Proceedings of the International Society for Magnetic Resonance in Medicine, ISMRM, 25th Annual Meeting and Exhibition, Honolulu, HI, USA; No. 4328; XP040691896; 2017.
European Search Report dated Feb. 11, 2019, for Application No. 18186548.6.

* cited by examiner

MAGNETIC RESONANCE DEVICE AND METHOD FOR PRODUCING A DIFFUSION GRADIENT COIL

CROSS-REFERENCE TO RELATED APPLICATIONS

The present application claims the benefit of the filing date of European patent application no. EP18186548, filed on Jul. 31, 2018, the contents of which are incorporated herein by reference in their entirety.

TECHNICAL FIELD

The disclosure relates to a magnetic resonance device comprising a patient receiving zone, at least one diffusion gradient coil, at least one magnet for generating a basic magnetic field, and a plurality of gradient coils for generating gradient fields overlaying the basic magnetic field. The basic magnetic field extends substantially along a first direction in the patient receiving zone and a first gradient of a first gradient field runs in the first direction and at least one further gradient of a further gradient field runs in a further direction orthogonal to the first direction. The diffusion gradient coil has at least one conductor loop running in one plane or a plurality of conductor loops each running in respective parallel planes. The disclosure further relates to a method for producing a diffusion gradient coil.

BACKGROUND

In magnetic resonance (MR) imaging, a diffusion gradient coil serves to generate a strong magnetic field locally by means of a diffusion pulse, in addition to the gradient fields generated by the gradient coils, which magnetic field strength is generated instead of or in addition to a diffusion gradient generated by the gradient coils. For this purpose, the diffusion gradient coil is positioned in the patient receiving zone and can at least partially enclose in particular a part of a patient's body, for example the head. Because of the comparatively small dimensions of the diffusion gradient coil, the spatial distribution of the field of the diffusion gradient coil will not generate a linear gradient, but will exhibit a strong local variation.

SUMMARY

In terms of the interactions with the other components of the magnetic resonance device, a diffusion gradient coil faces similar demands to those that are imposed on the gradient coils of the magnetic resonance device. Due to the arrangement of the diffusion gradient coil in the magnetic resonance device, however, further problems may arise during its use.

As a result of the interaction of the currents in the diffusion gradient coil with the basic magnetic field of the magnetic resonance device, torques can be produced that act on the diffusion gradient coil. The movements of the diffusion gradient coil resulting from these torques can be perceived as unpleasant for the patient. If strong rotational movements of the diffusion gradient coil take place due to the torques, then vibration-induced eddy currents can be formed in parts of the magnetic resonance device, and can interfere with the imaging being performed by the magnetic resonance device.

Furthermore, the diffusion gradient coil is exposed during its use to the fields of the gradient coils, in which case voltages can be induced reciprocally in the coils due to the variation with time of the gradient fields and/or of the diffusion gradient field generated by the diffusion gradient coil. As of a certain level of said induced voltages, this can lead to faults during operation, such as the occurrence of voltage spikes, for example, or even to failure of amplifiers connected to the respective coils. If a flow of current also results due to the coupled-in voltages, then eddy currents, and in particular those induced in the diffusion gradient coil, can lead to a heating of the diffusion gradient coil as well as to field disturbances. Particularly when a diffusion gradient coil is placed in or close to the field of view of the magnetic resonance device, even small eddy currents can lead to disturbances that degrade image quality.

The object underlying the embodiments described in the present disclosure addresses these issues by implementing a magnetic resonance device having a diffusion gradient coil that reduces or avoids malfunctions or sources of disturbance occurring during operation of the diffusion gradient coil.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. The drawing in which an element first appears is typically indicated by the leftmost digit(s) in the corresponding reference number.

DETAILED DESCRIPTION

The embodiments described herein are directed to a diffusion gradient coil that is arranged in an installation position in the patient receiving zone in such a way that the plane or planes of the conductor loops is or are oriented orthogonally to the first gradient and the conductor loop runs, or the conductor loops run in relation to the at least one further gradient field in its plane or their respective planes in such a way that a current induced in the diffusion gradient coil due to a variation with time of the at least one further gradient field and/or a torque generated by the basic magnetic field and acting on the diffusion gradient coil are/is canceled or substantially canceled. As used herein, the terms "canceled" or substantially canceled" will be understood as meaning that the respective values the terms describe are completely canceled or are canceled to within a certain threshold value such as being 90% canceled, 95% canceled, 99% canceled, etc.)

The magnetic resonance device can comprise in particular a cylindrical patient receiving zone along whose longitudinal axis, which is referred to in the following as the Z-axis, the basic magnetic field generated by the magnet of the magnetic resonance device extends. For spatial encoding purposes, a magnetic resonance device typically comprises at least three gradient coils, these generating a first gradient field having a gradient extending in the first direction of the basic magnetic field, i.e. in the Z-direction, as well as two further gradient fields, whose further gradients are oriented both orthogonal to the first direction and orthogonal to each other. The directions of the further gradients are in this case referred to in the following as the X-direction and the Y-direction.

The diffusion gradient coil may be comprised of one or more conductor loops. The conductor loops can in this case be connected to one another to form one or more coil units of the diffusion gradient coil. By different configuration of conductor loops of said type it is possible to generate different field profiles that are to be generated by the diffusion gradient coil, such as focusing fields, for example.

The advantage of the solution according to the disclosure is that, owing to the arrangement of the diffusion gradient coil in the patient receiving zone, undesirable effects and disturbances during the operation of the diffusion gradient coil or the magnetic resonance device can be reduced and/or prevented. To that end, the diffusion gradient coil is positioned in the installation position in which the plane or planes of the conductor loops of the diffusion gradient coil is or are oriented orthogonally to the first gradient. This means that a longitudinal axis of the diffusion gradient coil extends in the Z-direction, and that the conductor loop or conductor loops of the diffusion gradient coil runs or run orthogonally thereto, i.e. in an XY plane in each case.

It is furthermore provided in the installation position that the conductor loops run in relation to the at least one further gradient field in their respective planes in such a way that effects generated by at least one of the further gradient fields or due to a variation with time of at least one of the further gradient fields are canceled or substantially canceled. Taking into account the profile of the at least one further gradient field as well as the number and the shape of the conductor loops of the diffusion gradient coil, it is therefore possible to achieve a symmetrical or substantially symmetrical penetration of the diffusion gradient coil by the at least one further gradient field in the installation position, such that a current induced in the diffusion gradient coil due to a variation with time of the further gradient field and/or a torque generated by the basic magnetic field and acting on the diffusion gradient coil are/is canceled or substantially canceled.

Substantially cancel is to be understood in this context in the sense that e.g. the sum of two components of a current or a torque which act on the diffusion gradient coil or flow in the latter have different signs, with the result that the sum amounts for example to only 20% or 10% of the absolute value of one of the components. The torque acting on the diffusion gradient coil, or the current flowing in the diffusion gradient coil, can therefore be wholly or partially compensated, so that the effects on the diffusion gradient coil, such as movements, vibrations and/or heating, etc., and consequently the effects on a patient or on the gradient coils, are also advantageously reduced.

A variation with respect to time of the at least one gradient field can occur, for example, during the readout of image data as a result of the spatial encoding commonly used in magnetic resonance devices and/or when an echo-planar imaging (EPI) readout gradient typically employed in diffusion imaging is used. In such a case, a current can be induced in the diffusion gradient coil due to the time-varying magnetic field strength or flux density of the at least one further gradient field.

A torque can occur in the diffusion gradient coil when a current flows in the latter, for example in order to generate the diffusion gradient field. Owing to the orthogonal alignment of the conductor loop or conductor loops of the diffusion gradient coil with respect to the basic magnetic field, the current flow in this case causes Lorentz forces to be produced which act in the plane of the conductor loop or conductor loops of the diffusion gradient coil. In the conductor loop extending in one plane, there is in this case, on account of its loop shape, a spatially-separate current in one direction and a spatially-separate current in the opposite direction. Thus, as a result of the basic magnetic field, Lorentz forces acting on the conductor loops are produced in opposite directions in the plane of the conductor loop or conductor loops, which generate no or substantially no torque acting on the diffusion gradient coil. As used herein, the terms "no," "substantially no" torques may be understood as meaning zero or only small torques, e.g., a fraction of the ordinary torque that would otherwise be present such as 1% or less, 5%, 10%, etc.)

In a conductor loop lying in the XY plane, the at least one further gradient field can induce a current only by means of its component $B_Z$ extending in the Z-direction, because only $B_Z$ can penetrate through the surface area of the conductor loop. The intrinsic property of a gradient field is that $B_Z$ has the shape of a gradient, i.e. that the component $B_{Z,X}$ of a gradient field with a gradient extending in the X-direction has an identical amplitude at positions $+X_0$ and $-X_0$, for example, but a different sign. A current induced due to a variation with time of a further gradient field having a gradient extending in the X-direction can therefore self-compensate in the case of a corresponding arrangement of the conductor loop in relation to the gradient field. This of course applies analogously in the case of a further gradient field having a gradient extending in the Y-direction for the component $B_{Z,Y}$ at the positions $+Y_0$ and $-Y_0$.

As a result of the inventive arrangement of a diffusion gradient coil, torques and injections in the form of induced currents or voltages acting on the diffusion gradient coil are advantageously avoided. Advantageously, therefore, unpleasant sensations or even a risk to the patient, as well as damage to the hardware, in particular to amplifiers connected to the diffusion gradient coil and/or the gradient coils of the magnetic resonance device, can be avoided.

A diffusion gradient coil whose longitudinal axis runs parallel to the direction of the basic magnetic field or whose conductor loop or conductor loops is or are positioned orthogonally to the direction of the basic magnetic field, is furthermore particularly effective because the complete conductor length of the conductor loop or conductor loops of the diffusion gradient coil primarily generates a field component in the direction of the basic magnetic field, i.e. a $B_Z$ field or a useful field that can advantageously be used for imaging by means of the magnetic resonance device. These, similarly to a standard gradient extending in the Z-direction, are more efficient than transverse gradients, i.e. gradients running in the X- or Y-direction. By this means, the greatest field amplitudes of the field generated by the diffusion gradient coil are advantageously directed onto the target object, where they are required for the imaging in any case. Large field components in a direction orthogonal to the Z-direction can therefore be avoided, as a result of which undesirable interactions with the patient, such as peripheral nerve stimulation (PNS) in a neighboring region of the patient's body, can be prevented. The arrangement of the conductor loop or conductor loops in the XY plane is furthermore entirely feasible for common examinations performed using a diffusion gradient coil, such as on the patient's head or prostate, for example, since for this purpose the patient is usually positioned along the Z-direction in the magnetic resonance device.

According to the embodiments of the present disclosure, it can be provided that the diffusion gradient coil is oriented in relation to the first gradient field in such a way that a torque generated by the first gradient field and acting on the diffusion gradient coil and/or a current induced in the diffusion gradient coil due to a variation with time of the first gradient field are/is canceled or substantially canceled. This means that not only is the diffusion gradient coil positioned orthogonally to the Z-direction in such a way that no or substantially no disturbances occur due to one or more further gradient fields, but in addition the diffusion gradient coil is arranged in the installation position in the first direction, i.e. the Z-direction, in such a way that a torque generated by the first gradient field and acting on the diffusion gradient coil and/or a current induced in the diffusion gradient coil due to a variation with time of the first gradient field are/is canceled or substantially canceled.

The arrangement of the diffusion gradient coil in the installation position is accomplished in such a way that both a torque generated by the basic magnetic field and a current induced due to a variation with time of the first gradient field are canceled or substantially canceled and that induced currents are compensated for, as described hereinabove, for at least two further gradient fields whose gradients are oriented orthogonally to each other and orthogonally to the gradient of the first gradient field. In this way, all torques acting on the diffusion gradient coil or all currents induced in the diffusion gradient coil can advantageously be reduced or compensated for, such that overall no act on the diffusion gradient coil and no or only small currents (e.g., less than a current threshold of a current level ordinarily otherwise present such as 1%, 5%, 10%, etc.) are induced in the diffusion gradient coil.

In an embodiment, it can be provided that a conductor loop of the diffusion gradient coil and/or all conductor loops of the diffusion gradient coil are/is arranged symmetrically around an isocenter of the gradient fields. What is to be understood by the isocenter in this context is the point in the patient receiving zone at which a polarity reversal of the $B_Z$ component of the first gradient field and of the at least one further gradient field takes place. This means that in the isocenter the $B_Z$ component of the first and of the at least one further gradient field is zero in each case. In the case of a first gradient field running symmetrically along the first direction, the isocenter is consequently the midpoint of the first gradient field. In a conductor loop which is arranged through the isocenter in the XY plane, i.e. through the point Z=0 in the XY plane, no injection through the first gradient field takes place because there is no $B_Z$ component of the first gradient field there.

A diffusion gradient coil comprising a single conductor loop can therefore be arranged symmetrically around the isocenter in such a way that said one conductor loop is arranged in the XY plane through the isocenter of the first gradient field. A diffusion gradient coil comprising more than one conductor loop can in this case be arranged in such a way that the conductor loops are disposed symmetrically around the isocenter, such that overall the effect on the diffusion gradient coil due to the first gradient field is compensated for or substantially compensated for. With a range of conductor loops connected in series, what can therefore be achieved is that, in total, all positive and all negative injections into the diffusion gradient coil cancel one another out. The diffusion gradient coil may consist in particular of conductor loops each running in the Z-direction in an XY plane at different positions, a global effective center point of the diffusion gradient coil at which a symmetry exists in terms of the $B_Z$ components of the first and/or of the at least one further gradient field being located in the isocenter of the first gradient field, with the result that occurring torques and/or induced currents are at least substantially compensated for.

According to the embodiments described herein, it can be provided that the diffusion gradient coil comprises a plurality of conductor loops, the conductor loops being arranged concentrically and/or in each case offset along the longitudinal axis of the diffusion gradient coil and/or in each case having different diameters. It is particularly preferred in this case if the conductor loops of the diffusion gradient coil are symmetrical in relation to a center point of the diffusion gradient coil, since this simplifies the arrangement of the diffusion gradient coil in the installation position in particular in the case of symmetrical gradient fields.

For the conductor loop or conductor loops, it can be provided according to the embodiments of the disclosure that the conductor loops have a round, oval, rectangular, or polygonal planar cross-section. It can also be provided with regard to the shape of the conductor loops that these possess a symmetry in relation to a central axis of the diffusion gradient coil when the diffusion gradient coil is to be used with a symmetrical first gradient field and/or symmetrical further gradient fields in a magnetic resonance device. With gradient fields having sections that are asymmetrical, it is possible to compensate for the effect of an asymmetry of one or more of the gradient fields by means of corresponding differences in the profile and/or in the cross-sectional shape of one or more conductor loops of the diffusion gradient coil, such that even in the case of a section-wise asymmetrical first gradient field and/or asymmetrical further gradient fields, an arrangement of the diffusion gradient coil in the installation position provided according to the embodiments of the disclosure is possible owing to the profile of one or more conductor loops having been modified to match the asymmetry.

In an embodiment, it can be provided that the diffusion gradient coil is embodied for performing a measurement directed at the head and/or prostate of a patient positioned in the patient receiving zone. For this purpose, the diffusion gradient coil has an extension in the longitudinal direction and a diameter of the conductor loops that enables the diffusion gradient coil to be arranged at the head and/or in the region of the prostate of the patient. For a measurement targeting the prostate of a patient, the diffusion gradient coil can be positioned for example between the patient's thighs. For a measurement targeting the head of the patient, it can be provided that the diffusion gradient coil is positioned wholly or in sections around the head of the patient.

According to the embodiments of the disclosure, it can be provided that the magnetic resonance device has at least one retainer embodied in the patient receiving zone and/or in a patient support and positioning device arranged or arrangeable in the patient receiving zone to enable the diffusion gradient coil to be accommodated in a removable and play-free manner in the installation position. The formation of the first gradient field and the at least one further gradient field of the magnetic resonance device results from the gradient coils of the magnetic resonance device. In this case at least one retainer embodied in the patient receiving zone and/or on the patient support and positioning device can be provided in each case for one or more of the diffusion gradient coils assigned to the magnetic resonance device, in which retainer the diffusion gradient coils assigned to the magnetic resonance device can be arranged in their respective installation position.

The diffusion gradient coils are arranged in the retainer in this case in such a way that the diffusion gradient coils can be removed from the retainer when they are not required. Furthermore, the diffusion gradient coils are accommodated in the retainer with zero play (e.g., movement within a tightly defined tolerance less than a threshold value such less than a mm, for instance), thereby enabling a maximally exact positioning of the diffusion gradient coil in the installation position. For example, it is possible that a retainer is provided to receive a diffusion gradient coil embodied for performing a measurement in the head region of a patient and/or a further retainer is provided to receive a diffusion gradient coil embodied for performing a measurement in the prostate region of the patient. It is of course possible that still further and/or different retainers are also provided for the diffusion gradient coil in the patient receiving zone and/or on the patient support and positioning device for further examination purposes.

For the retainer, it can be provided according to an embodiment that this is implemented to accommodate the diffusion gradient coil in a positive-locking manner and/or that the retainer has mating parts corresponding to fastening means of the diffusion gradient coil. The retainer can be embodied for example as a recess in an inner lining of the patient receiving zone and/or in the patient support and positioning device, into which the diffusion gradient coil can be inserted. It is not necessary in this case for the whole diffusion gradient coil to be accommodated in the recess, but rather it suffices if a section thereof, for example a part of its external boundary, engages in the recess in a positive-locking manner such that a removable and play-free arrangement of the diffusion gradient coil in the retainer is given. Additionally or alternatively, it is possible that the retainer has mating parts corresponding to fastening means, such as, for example, bolts or studs of the diffusion gradient coil to enable the diffusion gradient coil to be screwed and/or affixed to the retainer.

According to embodiments of the disclosure, it can be provided that the magnetic resonance device comprises a patient support and positioning device, the first direction extending orthogonally or parallel to a patient support and positioning surface of the patient support and positioning device and the diffusion gradient coil being arranged in or on the patient support and positioning device. In a first direction, (e.g., the Z-direction), which extends parallel to a patient support and positioning surface of the patient support and positioning device, i.e. which therefore runs in a horizontal direction in particular inside a patient receiving zone of the magnetic resonance device, a diffusion gradient coil is arranged in such a way that the longitudinal axis of the diffusion gradient coil is likewise parallel to the first direction. This means that the planes in the conductor loop are arranged orthogonally to the patient support and positioning surface of the patient support and positioning device.

In the case of an open MR device, the first direction, i.e. the direction of the basic magnetic field, generally runs orthogonally to the patient support and positioning surface of the patient support and positioning device such that a diffusion gradient coil is arranged in such a way that the planes of the conductor loops of the diffusion gradient coil run parallel to the patient support and positioning surface of the patient support and positioning device, i.e. the longitudinal axis of the diffusion gradient coil is therefore oriented orthogonally to the patient support and positioning surface of the patient support and positioning device. The geometry in an open MR device is different compared with a conventional magnetic resonance device only in that the arrangement of the diffusion gradient coil in relation to the patient support and positioning surface of the patient support and positioning device or, as the case may be, to the patient, is different.

It can furthermore be provided according to an embodiment that at least one connection means connected to the diffusion gradient coil, e.g. an electric cable or a coolant hose, and/or at least one sensor assigned to the diffusion gradient coil are/is arranged in the patient support and positioning device. In this case, it can be provided that the at least one connection means is arranged in the vicinity of the retainer for the diffusion gradient coil such that a connection of the diffusion gradient coil is established when the latter is inserted into the retainer. An electric cable running in the patient support and positioning device can serve for example for supplying power to the diffusion gradient coil. A coolant, such as an oil for an oil cooling system for instance, can be supplied for example to the diffusion gradient coil by way of a coolant hose. An oil cooling of the diffusion gradient coil offers the advantage in this case that no additional water is introduced into the receiving zone of the magnetic resonance device. A, at least one sensor assigned to the diffusion gradient coil can also be arranged in the patient support and positioning device. The sensor can be used for example for current measurement and/or for a temperature measurement and/or for measurement of a diffusion gradient field generated by the diffusion gradient coil.

In an embodiment, a method for producing a diffusion gradient coil in accordance with the magnetic resonance device embodiments is provided using an optimization algorithm to determine the profile and/or the cross-sectional shape of the at least one conductor loop of the diffusion gradient coil and/or the arrangement of a plurality of conductor loops of the diffusion gradient coil relative to one another as a function of the at least one further gradient field generated by the gradient coils of the magnetic resonance device and as a function of the position of the diffusion gradient coil in the patient receiving zone, a minimization of a current induced in the diffusion gradient coil due to a variation with time of the at least one further gradient field being used as an optimization condition of the optimization algorithm.

In this way it is advantageously made possible for the diffusion gradient coil to be optimized for the use of a magnetic resonance device by means of the optimization of the profile and/or of the cross-sectional shape of the at least one conductor loop of the diffusion gradient coil, that is to say that when the diffusion gradient coil is arranged in its installation position in the magnetic resonance device, the effect of currents induced in the diffusion gradient coil by the at least one further gradient field can advantageously be reduced or avoided. The profile and/or the cross-sectional shape of the at least one conductor loop are/is determined with the aid of an optimization algorithm, with the minimization of a current induced in the diffusion gradient coil due to a variation with time of the at least one further gradient field being used as the optimization condition for the algorithm.

It is of course possible that further optimization conditions and/or boundary conditions can be specified for the algorithm. A maximum field strength to be reached by the diffusion gradient field and/or a gradient strength and/or a geometry of the diffusion gradient field can be used as a further optimization condition, for example in accordance with the purpose for which the diffusion gradient coil is to be used. As examples of a boundary condition, a number of conductor loops of the diffusion gradient coil, and/or a minimum diameter of the individual conductor loops of the diffusion gradient coil can be specified, thereby ensuring that the optimization result can also be used for specific examination purposes. It is also possible for the optimization to be performed for two further gradient fields having gradients in particular oriented orthogonally to each other and orthogonally to the direction of the basic magnetic field.

In addition, it can be provided according to an embodiment that a minimization of a torque generated by the first gradient field and acting on the diffusion gradient coil and/or of a current induced in the diffusion gradient coil due to a variation with time of the first gradient field is used as an additional optimization condition. In this way, it can be ensured that no or only minor negative effects on the diffusion gradient coil and/or on measurements performed with the aid of the diffusion gradient coil are caused even by a first gradient field having a first gradient running in the direction of the basic magnetic field.

Figure 1:
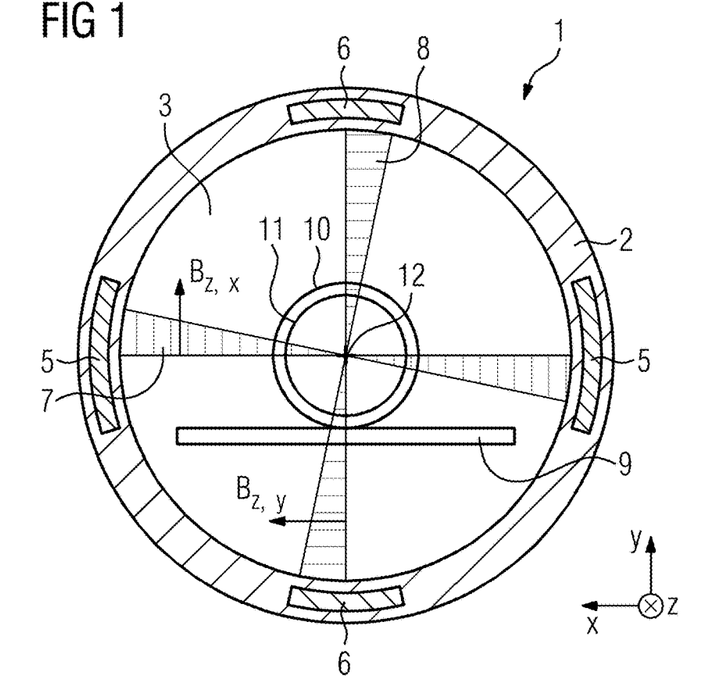
FIG. 1 shows a schematic front view of a first exemplary magnetic resonance device according to an embodiment of the disclosure.
Figure 2:
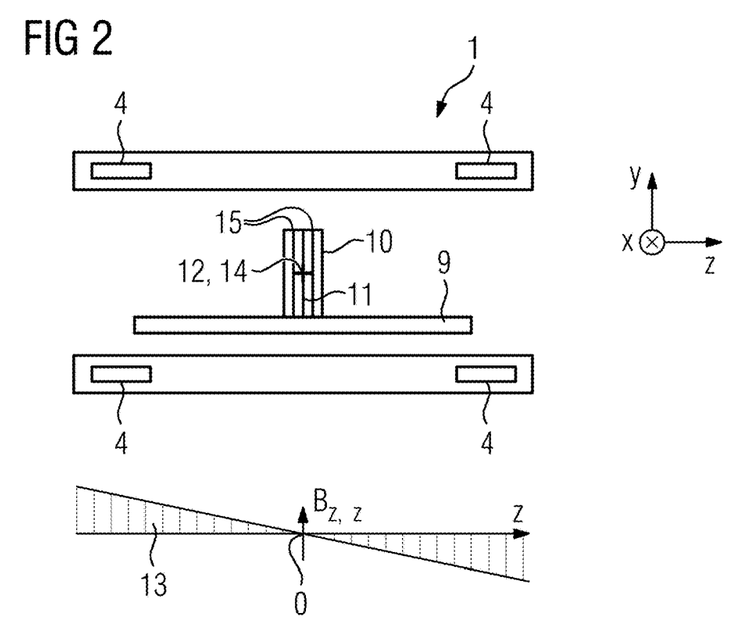
FIG. 2 shows a schematic side view of the first exemplary magnetic resonance device according to an embodiment of the disclosure.

FIG. 1 shows a schematic front view of a first exemplary magnetic resonance device according to an embodiment of the disclosure. This comprises a cylinder-shaped housing 2 laterally enclosing a patient receiving zone 3 embodied as a bore. The magnetic resonance device 1 also comprises a magnet (not shown in FIG. 1) for generating a basic magnetic field which in FIG. 1 extends into the drawing plane, that is to say along the Z-axis. In addition, the magnetic resonance device 1 comprises a plurality of gradient coils 4, 5, 6, which serve to generate gradient fields overlaying the gradient field. The gradient coils 4 serve to generate a first gradient field whose first gradient extends along the basic magnetic field extended in the Z-direction. The gradient coils 4 are represented schematically in FIG. 2, which shows a side view of the magnetic resonance device 1 according to an embodiment. FIG. 1 shows a schematic view of the gradient coils 5, which serve to generate a further gradient field having a further gradient, in this case running (i.e., being disposed or situated) in the X-direction. A further gradient field, whose further gradient extends in the Y-direction, is generated similarly by the gradient coils 6. The arrangement and shape of the gradient coils 4, 5, 6 in FIGS. 1 and 2 is for clarity of illustration and ease of explanation, and thus is purely by way of example and not limitation.

The profile of the Z component $B_{Z,X}$ of the further gradient field having the further gradient extending in the X-direction is represented schematically in the graph 7, while the graph 8 similarly shows the Z component $B_{Z,Y}$ of the further gradient field having the further gradient extending in the Y-direction. The further gradient extending in the X-direction and the further gradient extending in the Y-direction are both orthogonal to each other and orthogonal to the first gradient of the first gradient field extending in the Z-direction.

Also represented schematically in the interior of the patient receiving zone 3 are a patient support and positioning device 9, which can be embodied for example as a couch, and a diffusion gradient coil 10. The diffusion gradient coil 10 comprises one or more conductor loops 11, each of which extends in an XY plane. Where there are multiple conductor loops 11, the respective XY planes in which the conductor loops extend are parallel and spaced apart from one another in the Z-direction. In this embodiment, the conductor loops 11 of the diffusion gradient coil 10 have a circular cross-section and a constant diameter. A conductor loop 11 of the diffusion gradient coil 10 is represented schematically in FIG. 1.

The diffusion gradient coil 10 is arranged in an installation position in the patient receiving zone 3 in such a way that the conductor loop 11 is in an orthogonal orientation with respect to the first gradient extending in the Z-direction or, as the case may be, to the basic magnetic field. Furthermore, the conductor loop 11 is arranged in its plane in such a way that it is oriented, both relative to the further gradient running in the X-direction and relative to the further gradient running in the Y-direction, symmetrically with respect to an axis of symmetry 12 of the further gradient fields, i.e. the center point of the circular conductor loop 11 lies on the axis of symmetry 12. The axis of symmetry 12 describes the axis for which the further gradient fields running symmetrically in each case in the X-direction and Y-direction have no Z component $B_{Z,X}$ and $B_{Z,Y}$, respectively. Owing to the symmetrical embodiment of the further gradient fields in the X- and Y-direction, the axis of symmetry 12 shown in the schematic in FIG. 1 coincides with the centerline of the patient receiving zone 3 or the magnetic resonance device 1. If there is an asymmetry in one or both of the further gradient fields, the axis of symmetry 12 can be a curve and have a profile diverging from a straight line, for instance from the centerline of the patient receiving zone 3.

Owing to the symmetrical arrangement of the conductor loop 11 around the axis of symmetry 12 and the symmetrical profile of the Z components $B_{Z,X}$ and $B_{Z,Y}$ around the axis of symmetry 12, a current induced in the conductor loop 11 of the diffusion gradient coil 10 by means of the Z components $B_{Z,X}$ and $B_{Z,Y}$ due to a variation with time of one of the further gradient fields is canceled or substantially canceled.

FIG. 2 shows a schematic side view of the first exemplary magnetic resonance device according to an embodiment of the disclosure. The profile of the Z component $B_{Z,Z}$ of the first gradient field, which is generated by the gradient coils 4, is represented schematically in the graph 13. The diffusion gradient coil 10 is arranged symmetrically around an isocenter 14 of the first gradient field having the first gradient extending in the Z-direction. The isocenter 14 describes the point at which the XY plane coincides with the axis of symmetry 12 of the further gradient fields at the position at which the Z component $B_{Z,Z}$ of the first gradient field is zero. The symmetrical arrangement is achieved in that the middle conductor loop 11 of the three conductor loops 11, 15 of the diffusion gradient coil 10 runs through the isocenter 14 and the other two conductor loops 15 are arranged spaced apart therefrom on both sides of the isocenter 14, the three conductor loops 11, 15 each extending orthogonally to the Z-direction in the XY plane. No injection of the gradient fields generated by the gradient coils 4, 5, 6 into the diffusion gradient coil 10 takes place in the XY plane, which runs directly through the isocenter 14. The injections into the conductor loops 15, which are spaced apart from the isocenter 14 in both Z-directions, each have an opposite sign and thus cancel each other out completely or substantially completely (e.g., within a threshold level of cancellation such as 90%, 95%, 99%, etc.). Negative effects for a patient positioned on the patient support and positioning device 9, such as, for example, a vibration and/or a heating of the diffusion gradient coil 10, can therefore advantageously be avoided.

Figure 3:
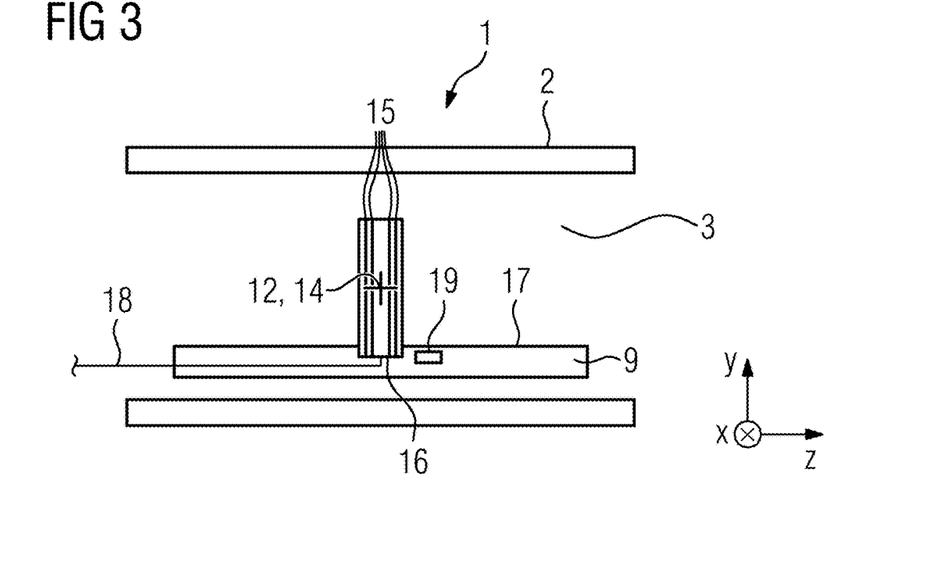
FIG. 3 shows a schematic side view of a second exemplary magnetic resonance device according to an embodiment of the disclosure.

FIG. 3 shows a schematic side view of a second exemplary magnetic resonance device according to an embodiment of the disclosure. In this embodiment, the diffusion gradient coil 10 comprises four conductor loops 15, which are arranged symmetrically around the isocenter 14. The arrangement of the conductor loops 15 in relation to the axis of symmetry 12 of the further gradients of the further gradient fields extending in the X-direction or Y-direction is analogous to the arrangement of the conductor loop 11 with respect to the axis of symmetry 12 of the schematic shown in FIG. 1. To achieve a precise positioning of the diffusion gradient coil 10 in the installation position shown in FIG. 3, the patient support and positioning device 9 has a holding fixture 16 into which the diffusion gradient coil 10 is inserted in a positive-locking and play-free manner. In this context, "play-free" may mean secured and fixedly mounted (although still installed in a removable manner) and having a threshold amount of movement or play in each direction (e.g., the X, Y, and Z-axes) once installed. For example, play-free may mean having movement in each axis of less than a millimeter or a fraction thereof (e.g., 0.01 mm, 0.1 mm, 0.5 mm, etc.)

In this arrangement, the retainer 16 is embodied as a pocket or recess in a patient support and positioning surface 17 of the patient support and positioning device 19. Additionally or alternatively, the retainer 16 can also comprise mating parts corresponding to fastening means of the diffusion gradient coil 10, such as, for example, one or more threads for receiving bolts and/or one or more recesses for receiving studs and/or feet of the diffusion gradient coil 10. With the diffusion gradient coil 10 disposed in the retainer 16, the diffusion gradient coil 10 is arranged in relation to the first and the further gradient fields in such a way that torques generated in the coil both by the first gradient field and by the further gradient fields and/or currents induced in the diffusion gradient coil are canceled or substantially canceled.

The patient support and positioning device 9 additionally includes a line 18 that is connected to the diffusion gradient coil 10. The line 18 can be for example an electric cable and/or a coolant line for supplying a coolant, such as an oil for instance, to the diffusion gradient coil 10. A plurality of electric cables and/or fluidic lines can of course be provided and connected to the diffusion gradient coil 10 accommodated in the retainer 16. The patient support and positioning device 9 further comprises a sensor 19 assigned to the diffusion gradient coil 10 to serve, for example, for measuring a diffusion gradient field generated by the diffusion gradient coil 10 and/or a current through the diffusion gradient coil 10 and/or a temperature of the diffusion gradient coil 10. The sensor 19 can also be connected via connecting means (not shown here) to an evaluation means arranged outside of the patient receiving zone 3 and/or a computing device or any other suitable device in a similar manner.

Figure 4:
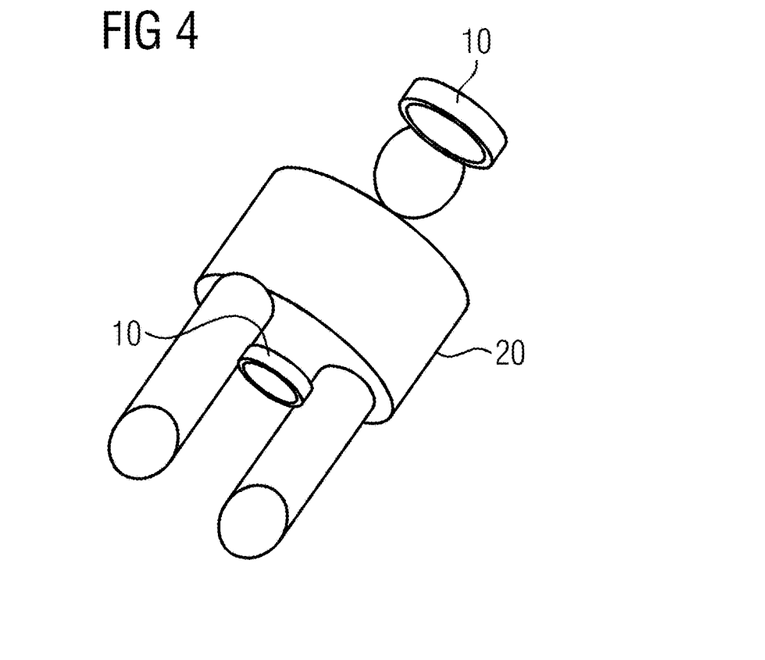
FIG. 4 shows a schematic representation of an arrangement of diffusion gradient coils on a patient according to an embodiment of the disclosure.

FIG. 4 shows a schematic representation of an arrangement of diffusion gradient coils on a patient according to an embodiment of the disclosure. Two diffusion gradient coils 10 are arranged on the patient 20. One diffusion gradient coil 10 is arranged around the head of the patient, while the other diffusion gradient coil is positioned between the thighs of the patient 20. The diffusion gradient coils 10 can be used according to their positioning for example for performing a measurement in the head region of the patient 20 and/or for performing a measurement in the prostate region of the patient 20. Depending on its deployment location, a diffusion gradient coil 10 can in this case have for example a different number of conductor loops 11 and/or conductor loops 15, as discussed above, having different diameters or different cross-sectional shapes.

Figure 5:
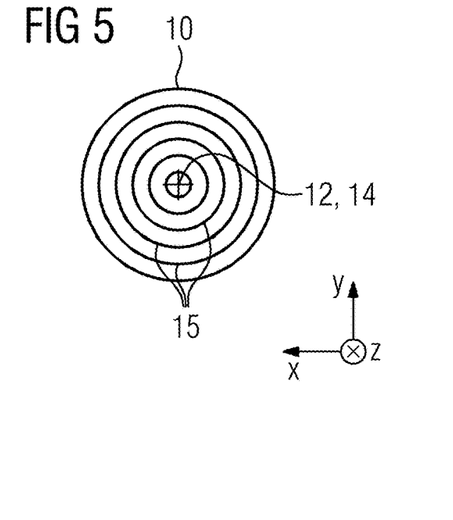
FIGS. 5-7 show different views of a diffusion gradient coil according to an embodiment of the disclosure.
Figure 6:
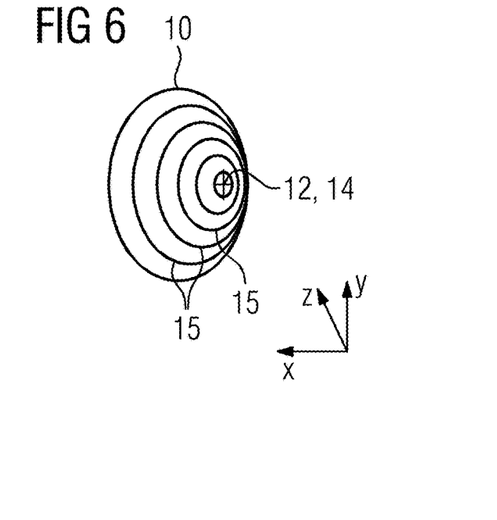
Figure 7:
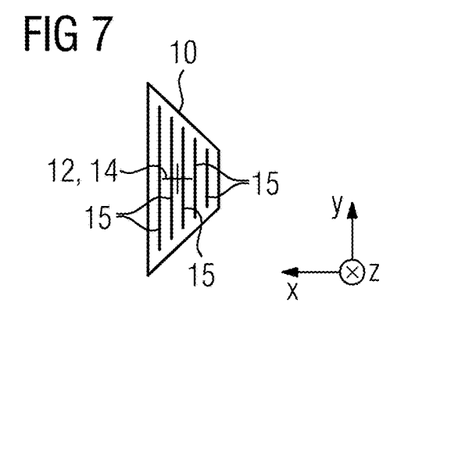

FIGS. 5-7 show different views of a diffusion gradient coil according to an embodiment of the disclosure. The diffusion gradient coil 10 comprises a plurality of circular, concentrically arranged conductor loops 15. The example shown in FIG. 5 shows the diffusion gradient coil 10 in the XY plane. The diffusion gradient coil 10 is in this case arranged around the isocenter 14 in such a way that all of the center points of the concentric circles in the XY planes coincide with the axis of symmetry 12. To clarify the arrangement, FIG. 6 further shows a view from an angle onto the diffusion gradient coil 10, while FIG. 7 shows the view of the diffusion gradient coil 10 in the YZ plane. It can be seen in FIG. 7 for example that the individual conductor loops 15 have different diameters. The diffusion gradient coil 10 is arranged around the isocenter 14 for example in such a way that three conductor loops 15 having a smaller diameter are arranged to the right of the isocenter 14, and two conductor loops 15 having a larger diameter are arranged on the other side of the isocenters, i.e. in the negative Z-direction. This arrangement around the isocenter 14 enables torques generated due to the first gradient field and/or currents induced in the diffusion gradient coil due to variations with time of said first gradient field to cancel one another out completely or substantially.

If the profile of the first gradient field and those of the further gradient fields of the magnetic resonance device are known, it is possible in a method according to an embodiment to determine the arrangement with respect to one another and/or the cross-sectional shape of the conductor loop 11 and/or of the conductor loops 15 of the diffusion gradient coil 10.

Figure 8:
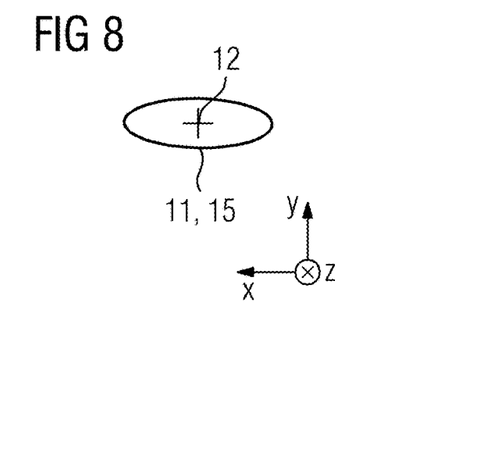
FIGS. 8-10 show schematic representations of different profiles of a conductor loop of a diffusion gradient coil according to an embodiment of the disclosure.
Figure 9:
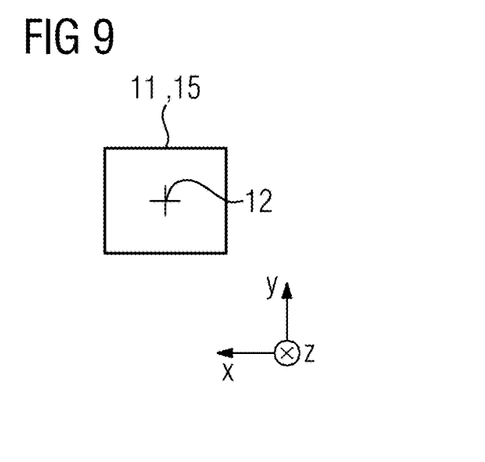
Figure 10:
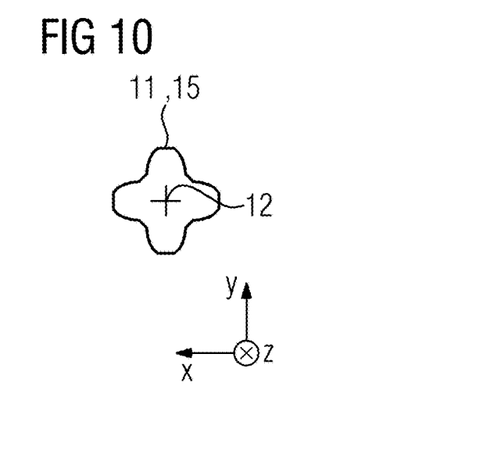

FIGS. 8-10 show schematic representations of different profiles of a conductor loop of a diffusion gradient coil according to an embodiment of the disclosure. For example, some example profiles or geometries for individual conductor loops 11, 15 are shown in FIGS. 8-10. To enable the individual conductor loops 11, 15 to be arranged orthogonally to the direction of the first gradient or of the basic magnetic field, it is provided for each of the conductor loops 11, 15 that these extend in a planar fashion in one plane, in this case the XY plane. The necessarily present thickness of a conducting material for forming the conductor loops 11, 15, as well as possibly provided connecting pieces which combine a plurality of conductor loops 11, 15 of the diffusion gradient coil into one or more coils, are not shown in these Figures for ease of explanation and clarity and not by way of limitation. The embodiments described herein may implement any suitable coil geometries, with some example geometries being an oval geometry, as shown in FIG. 8, a square geometry, as shown in FIG. 9, and a geometry with polygonal cross-section, as shown in FIG. 10.

Also shown in FIGS. 8-10 is the axis of symmetry 12 of each of the further gradient fields, the conductor loops 11 in each case being arranged symmetrically around said axis of symmetry 12. The method according to an embodiment enables the geometry of the conductor loop 11 and/or of the conductor loops 15 of the diffusion gradient coil to be optimized, a minimization of a current induced in the diffusion gradient coil 10 due to a variation with time of the at least one further gradient field and/or of a torque generated by the at least one further gradient field and acting on the diffusion gradient coil being used as optimization criterion.

It is of course also possible that the optimization algorithm is used for example to determine an arrangement of a plurality of conductor loops 15 in the Z-direction, as shown previously in FIG. 7 for example, with the aid of a further optimization criterion in terms of the first gradient field. A minimum required diameter of a conductor loop 11, 15, for example, or a number of conductor loops 11, 15 necessary to form the diffusion gradient coil can be used as boundary conditions for the optimization. With the aid of the method according to the embodiment, diffusion gradient coils 10 can therefore be produced which are assigned to a specific magnetic resonance device 1 or to a specific type of magnetic resonance devices 1 so that said coils can be arranged easily in the installation position in the patient receiving zone 3 of said magnetic resonance device 1 and in particular can be retained in a holding fixture 16.

Although the embodiments have been illustrated and described in more detail on the basis of example embodiments as shown herein, the disclosure is not limited by these examples, and other variations can be derived herefrom by the person skilled in the art without leaving the scope of protection of the disclosure.

What is claimed is:

1. A magnetic resonance device configured to generate a basic magnetic field, the magnetic resonance device comprising:
 a patient receiving zone;
 a diffusion gradient coil; and
 a plurality of gradient coils configured to generate gradient fields overlaying the basic magnetic field,
 wherein the generated basic magnetic field extends substantially along a first direction within the patient receiving zone,
 wherein the plurality of gradient coils are configured to generate a first gradient of a first gradient field disposed in the first direction, and a second gradient of a second gradient field disposed in a second direction that is orthogonal to the first direction, and
 wherein the diffusion gradient coil includes a conductor loop disposed in a conductor loop plane, the diffusion gradient coil being arranged within the patient receiving zone such that the conductor loop plane is oriented orthogonally to the first gradient of the first gradient field, and the conductor loop is disposed in relation to the second gradient field such that at least one of (i) a current induced in the diffusion gradient coil due to a variation with time of the second gradient field, and (ii) a torque generated by the basic magnetic field and acting on the diffusion gradient coil, is canceled.

2. The magnetic resonance device as claimed in claim 1, wherein the diffusion gradient coil is oriented relative to the first gradient field such that at least one of (i) a torque generated by the first gradient field acting on the diffusion gradient coil, and (ii) a current induced in the diffusion gradient coil due to a variation with time of the first gradient field, is canceled.

3. The magnetic resonance device as claimed in claim 1, wherein a conductor loop of the diffusion gradient coil is arranged symmetrically around an isocenter of the first gradient field.

4. The magnetic resonance device as claimed in claim 1, wherein the diffusion gradient coil has a plurality of conductor loops, and
 wherein each one of the plurality of conductor loops is arranged concentrically along a longitudinal axis of the diffusion gradient coil, each one of the plurality of conductor loops having a different diameter.

5. The magnetic resonance device as claimed in claim 1, wherein the diffusion gradient coil has a plurality of conductor loops, and
 wherein each one of the plurality of conductor loops is offset from a longitudinal axis of the diffusion gradient coil, each one of the plurality of conductor loops having a different diameter.

6. The magnetic resonance device as claimed in claim 1, wherein the conductor loop has a planar cross-section including one of a round, oval, rectangular, or polygonal shape.

7. The magnetic resonance device as claimed in claim 1, wherein the diffusion gradient coil is configured to perform a measurement in a head and/or prostate region of a patient positioned within the patient receiving zone.

8. The magnetic resonance device as claimed in claim 1, further comprising:
 a retainer disposed within the patient receiving zone and/or within a patient support and positioning device that is positioned within the patient receiving zone, the retainer being configured to enable the diffusion gradient coil to be removably installed in the patient receiving zone in a play-free manner.

9. The magnetic resonance device as claimed in claim 8, wherein the retainer is configured to enable installation of the diffusion gradient coil in a positive-locking manner and/or has mating parts corresponding to fastening components of the diffusion gradient coil.

10. The magnetic resonance device as claimed in claim 1, further comprising:
 a patient support and positioning device,
 wherein the first direction extends orthogonally or parallel to a surface associated with the patient support and positioning device, and
 wherein the diffusion gradient coil is arranged in or on the patient support and positioning device.

11. The magnetic resonance device as claimed in claim 1, further comprising:
 a patient support and positioning device; and
 at least one of (i) a sensor assigned to the diffusion gradient coil, or (ii) a connecting means connected to the diffusion gradient coil, is arranged in the patient support and positioning device.

12. The magnetic resonance device as claimed in claim 11, wherein the connecting means connected to the diffusion gradient coil includes an electric cable or a coolant hose.

13. The magnetic resonance device as claimed in claim 1, wherein the diffusion gradient coil has a plurality of conductor loops, each conductor loop from among the plurality of conductor loops being disposed in a respective parallel plane, and
 wherein the diffusion gradient coil is arranged within the patient receiving zone such that the parallel planes of the plurality of conductor loops are oriented orthogonally to the first gradient, and the plurality of conductor loops are disposed in their respective planes in relation to the second gradient field such that at least one of (i) a current induced in the diffusion gradient coil due to a variation with time of the second gradient field, and (ii) a torque generated by the basic magnetic field and acting on the diffusion gradient coil, is canceled.

14. A method for producing a diffusion gradient coil for a magnetic resonance device, the method comprising:
providing a patient receiving zone;
providing a diffusion gradient coil;
generating a basic magnetic field in accordance with the magnetic resonance device;
providing a plurality of gradient coils configured to generate gradient fields overlaying the basic magnetic field,
wherein the generated basic magnetic field extends substantially along a first direction within the patient receiving zone,
wherein the plurality of gradient coils are configured to generate a first gradient of a first gradient field disposed in the first direction, and a second gradient of a second gradient field disposed in a second direction that is orthogonal to the first direction, and
wherein the diffusion gradient coil includes a plurality of conductor loops, each conductor loop from among the plurality of conductor loops being disposed in a respective parallel plane, the diffusion gradient coil being arranged within the patient receiving zone such that the parallel planes of the plurality of conductor loops are oriented orthogonally to the first gradient, and the plurality of conductor loops are disposed in their respective planes in relation to the second gradient field such that at least one of (i) a current induced in the diffusion gradient coil due to a variation with time of the second gradient field, and (ii) a torque generated by the basic magnetic field and acting on the diffusion gradient coil, is canceled; and
executing an optimization algorithm to determine a profile and/or a cross-sectional shape of at least one conductor loop of the diffusion gradient coil and/or the arrangement of the plurality of conductor loops of the diffusion gradient coil relative to one another as a function of (i) the second gradient field, and (ii) the position of the diffusion gradient coil in the patient receiving zone,
wherein a minimization of a current induced in the diffusion gradient coil due to a variation with time of the second gradient field is used as an optimization condition of the optimization algorithm.

15. The method as claimed in claim 14, wherein the execution of the optimization algorithm includes the calculation of, as an additional optimization condition, a minimization of a torque generated by the first gradient field and acting on the diffusion gradient coil.

16. The method as claimed in claim 14, wherein the execution of the optimization algorithm includes the calculation of, as an additional optimization condition, a minimization of a current induced in the diffusion gradient coil due to a variation with time of the first gradient field.

* * * * *